United States Patent [19]
Snead

[11] Patent Number: 4,963,092
[45] Date of Patent: Oct. 16, 1990

[54] BUCCAL TUBE APPLICANCE FOR RECTANGULAR OR ROUND WIRE

[75] Inventor: Wilford A. Snead, San Dimas, Calif.

[73] Assignee: Unitek Corporation, Monrovia, Calif.

[21] Appl. No.: 344,893

[22] Filed: Apr. 28, 1989

[51] Int. Cl.⁵ .............................................. A61C 3/00
[52] U.S. Cl. ................................................... 433/17
[58] Field of Search ......................... 433/17, 18, 8, 16

[56] References Cited
U.S. PATENT DOCUMENTS
4,781,582  11/1988  Kesling .................................. 433/17

Primary Examiner—Cary E. Stone
Attorney, Agent, or Firm—Donald M. Sell; Walter N. Kirn; James D. Christoff

[57] ABSTRACT

An orthodontic buccal tube appliance for use with the molars has a tube with a mesial, open-ended cylindrical passage and a distal rectangular passage aligned with the cylindrical passage. The tube is thus adapted for use with either round or rectangular wire in accordance with the preference of the orthodontist. A funnel-shaped wall connects the cylindrical passage to the rectangular passage in order to guide an end of rectangular wire toward a position within the rectangular passage.

6 Claims, 1 Drawing Sheet

BUCCAL TUBE APPLICANCE FOR RECTANGULAR OR ROUND WIRE

BACKGROUND OF THE INVENTION

1. Field of the Invention

This invention relates to an orthodontic buccal tube adapted for use with wire having either a round or rectangular cross-section.

2. Description of the Related Art

During orthodontic therapy, buccal tubes are secured to the molar teeth to hold the ends of an arch wire in place. The arch wire is guided through slots in brackets fixed to anterior, cuspid and bicuspid teeth, and forms a track to guide the movement of the teeth.

Orthodontic arch wire typically has either a rectangular or round cross-section. Rectangular arch wire is useful when placed in brackets having matching rectangular slots so that the wire can apply torque to the brackets to accomplish certain movement of the teeth. On the other hand, it may be desirable to utilize round wire to accomplish movement of the teeth where torquing forces are not involved. In some instances, the orthodontist may use a round wire during earlier stages of treatment, and then switch to a rectangular wire at a later time.

The buccal tube may also have a passage for receiving an auxiliary wire such as headgear wire, a lip bumper or a segmented arch wire in addition to a channel for receiving the main arch wire. Typically, headgear wire and lip bumper wire have a round cross-section, while segmented arch wire has a rectangular cross-section. Consequently, if initial treatment includes headgear or a lip bumper which is later replaced with a segmented arch wire, the buccal tubes initially mounted on the molars for receiving round wires are often removed and replaced with buccal tubes adapted to receive rectangular wires. Such practice, however, is costly and time consuming. Another option is to utilize a double buccal tube appliance having a round tube and rectangular tube mounted side-by-side on a single base, but such an arrangement is too large in some cases and requires the ends of one of the wires to be bent to fit the offset between the two tubes.

A convertible buccal tube assembly is described in U.S. Pat. No. 4,781,582 and includes a cylindrical tube along with a flap having a rectangular opening. The flap may be bent to a position on the mesial side of the opening to the cylindrical tube so that torquing forces can be applied between rectangular arch wire and the buccal tube. The flap may also be bent to an out-of-the-way location in order to insert round wire into the cylindrical opening. However, the assembly described in U.S. Pat. No. 4,781,582 presents certain manufacturing difficulties and also requires some additional time and effort of the orthodontist whenever the arch wire is changed from round to rectangular or vice versa.

SUMMARY OF THE INVENTION

The present invention is directed toward a buccal tube appliance having a base and a tube connected to the base. The tube extends in a generally mesiodistal direction, and has an open-ended mesial end portion and a distal end portion immovably secured to the mesial end portion. The distal end portion has a rectangular passage for receiving a rectangular wire, and the mesial end portion has a passage leading from the rectangular passage and adapted to receive a round wire having a cross-section larger than the rectangular passage.

As a result, the buccal tube appliance is adapted for use with either round or rectangular wires, and yet does not require any effort of the orthodontist in converting the tube when switching from round to rectangular wire. Moreover, the provision of a single tube having both round and rectangular portions reduces the bulk of the appliance.

DESCRIPTION OF THE PREFERRED EMBODIMENT

Figure 1:
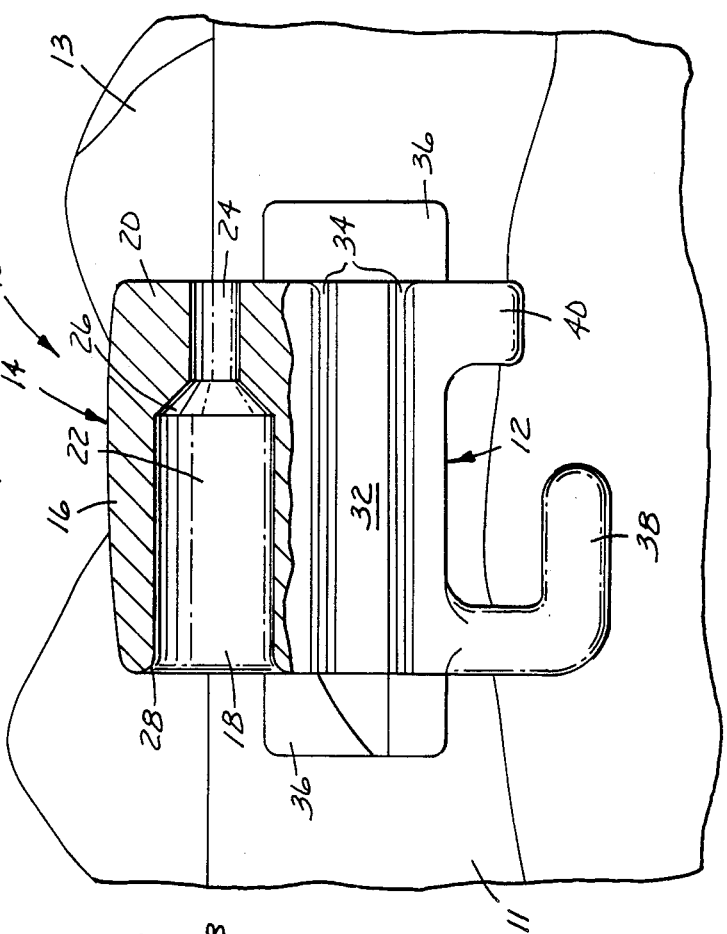
FIG. 1 is a labial view of a buccal tube appliance of the invention mounted on a first molar, with parts broken away in section to reveal adjoining internal wire passages.
Figure 2:
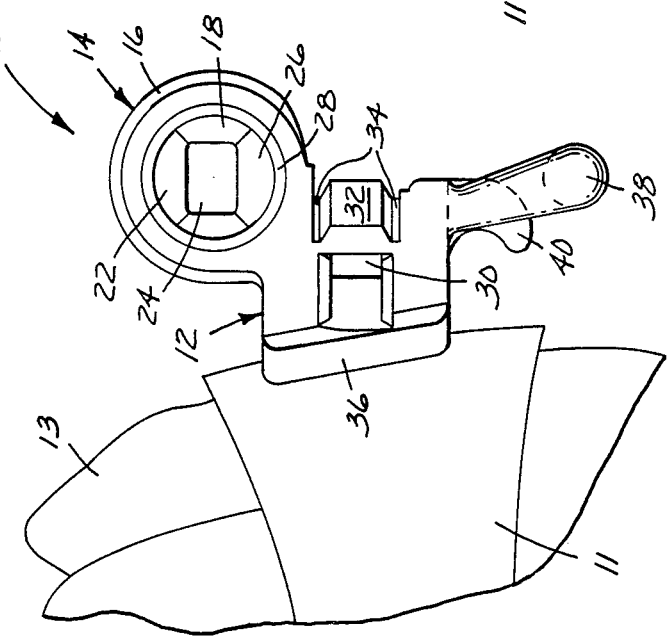
FIG. 2 is a view of a mesial end of the buccal tube appliance shown in FIG. 1.

A buccal tube appliance 10 is shown in FIGS. 1 and 2 and includes a base 12 that is mounted on a band 11 encircling a lower first molar 13, and that is integrally connected to a tube 14. The tube 14 extends in a generally mesiodistal direction, and includes a mesial end portion 16 having an open end 18, and a distal end portion 20 that is immovably secured to the mesial end portion 16. The mesial end portion 16 has a generally cylindrical passage 22 adapted to receive a round wire, while the distal end portion 20 has a rectangular passage 24 adapted to receive a rectangular wire. The rectangular passage 24 is coaxially aligned with the cylindrical passage 22.

Preferably, the tube 14 is formed with an internal, generally frustro-conical wall 26 which forms a funnel-shaped inlet leading from the cylindrical passage 22 to the rectangular passage 24. In addition, the open end 18 of the cylindrical passage 22 is rounded at 28 to facilitate insertion of a wire (not shown) into the passage 22. The length of the cylindrical passage 22 is preferably about three times the length of the rectangular passage 24.

The appliance 10 is also formed with a channel 30 that is rectangular in cross-section and which is at least initially covered by a cap 32 that may be sheared along two notches 34,34 in order to open the channel 30 in buccal directions. The appliance 10 has two end flanges 36,36 for welding the base 12 to bands or bonding pads, and a hook 38 along with a tie wing 40 are also provided for facilitating movement of the associated tooth in certain cases.

In use of the appliance 10, a main arch wire is placed in the channel 30 once the appliance 10 is secured to the molar 13. The cylindrical passage 22 of the tube 14 may be used to receive ends of a facebow that is part of headgear used to apply extraoral forces to the teeth. Alternatively, an intraoral appliance such as a lip bumper having cylindrical ends may be placed in the passage 22. At the discretion of the orthodontist, the facebow or lip bumper may be removed and an auxiliary, rectangular wire for segmented arch control may then be inserted into the tube 14 for applying torquing forces to the associated teeth. When using an auxiliary rectangular arch wire, the end is placed through the open end 18 of the tube 14, through the cylindrical mesial passage 22 and then is guided by the funnel-shaped wall 26 toward a position inside of the rectangular distal passage 24.

The longitudinal axis of the rectangular channel 30 for the main arch wire is side-by-side and oriented at a slight angle in relation to the common longitudinal axis of the aligned passages 22,24. However, the invention is also useful in appliances having only a single tube with a mesial cylindrical passage and an aligned, adjacent rectangular passage, both of which are adapted for use with the main arch wire.

I claim:

1. A buccal tube appliance having a base and a tube connected to said base, said tube extending in a generally mesiodistal direction and having an open-ended mesial end portion and a distal end portion integrally connected to said mesial end portion, said distal end portion being immovable relative to said mesial end portion and having a rectangular passage for receiving a rectangular wire, said mesial end portion having a passage leading from said rectangular passage and adapted to receive a round wire having a cross-section larger than said rectangular passage.

2. The appliance of claim 1, wherein said tube has a funnel-shaped wall leading from said passage of said mesial end portion to said rectangular passage.

3. The appliance of claim 1, wherein said passage of said mesial end portion and said passage of said distal end portion have a common longitudinal axis.

4. The appliance of claim 1, wherein said passage of said mesial end portion has a length that is about three times the length of said rectangular passage.

5. The appliance of claim 1 and including a rectangular main arch wire channel located in side-by-side relation to said passage of said mesial end portion and said rectangular passage.

6. The appliance of claim 1, wherein said passage of said mesial end portion is cylindrical.

* * * * *